United States Patent

Ocain et al.

[11] Patent Number: 5,385,910
[45] Date of Patent: Jan. 31, 1995

[54] GEM-DISTRIBUTED ESTERS OF RAPAMYCIN

[75] Inventors: Timothy D. Ocain, Framingham, Mass.; Guy A. Schiehser, Yardley, Pa.

[73] Assignee: American Home Products Corporation, Madison, N.J.

[21] Appl. No.: 156,334

[22] Filed: Nov. 22, 1993

[51] Int. Cl.⁶ .................. A61K 31/445; C07D 471/04
[52] U.S. Cl. ............................ 514/291; 540/456
[58] Field of Search .................... 540/456; 514/291

[56] References Cited

U.S. PATENT DOCUMENTS

| | | | |
|---|---|---|---|
| 3,929,992 | 12/1975 | Sehgal et al. | 542/122 |
| 3,993,749 | 11/1976 | Sehgal et al. | 424/122 |
| 4,316,885 | 2/1982 | Rakhit | 424/122 |
| 4,375,464 | 3/1993 | Sehgal et al. | 424/122 |
| 4,401,653 | 8/1983 | Eng | 424/122 |
| 4,650,803 | 3/1987 | Stella et al. | 514/291 |
| 4,885,171 | 12/1989 | Surendra et al. | 424/122 |
| 5,023,262 | 6/1991 | Caufield et al. | 514/291 |
| 5,023,263 | 6/1991 | Von Burg | 514/291 |
| 5,023,264 | 6/1991 | Caufield | 514/291 |
| 5,078,999 | 1/1992 | Warner et al. | 424/122 |
| 5,080,899 | 1/1992 | Sturm et al. | 424/122 |
| 5,091,389 | 2/1992 | Ondeyka et al. | 514/291 |
| 5,100,883 | 3/1992 | Schiehser | 514/183 |
| 5,100,899 | 3/1992 | Calne | 514/291 |
| 5,102,876 | 4/1992 | Caufield | 514/183 |
| 5,118,677 | 6/1992 | Caufield | 514/183 |
| 5,118,678 | 6/1992 | Kao et al. | 514/183 |
| 5,120,842 | 6/1992 | Failli et al. | 540/452 |
| 5,130,307 | 7/1992 | Failli et al. | 514/321 |
| 5,138,051 | 8/1992 | Hughes et al. | 540/456 |
| 5,151,413 | 9/1992 | Caufield et al. | 514/63 |
| 5,169,851 | 12/1992 | Hughes et al. | 514/291 |
| 5,177,203 | 1/1993 | Failli et al. | 540/456 |
| 5,194,447 | 3/1993 | Kao | 514/542 |
| 5,221,670 | 6/1993 | Caufield | 514/183 |
| 5,233,036 | 8/1993 | Hughes | 540/455 |

FOREIGN PATENT DOCUMENTS

507555A1 7/1992 European Pat. Off. ............ 540/456

OTHER PUBLICATIONS

Kao et al., Commonly owned U.S. Patent Application SN 08/054,655 Filed: Apr. 23, 1993.
Venzina, C., J. Antibiot. 28:721 (1975).
Sehgal, S. N., J. Antibiot. 28:727 (1975).
Baker, H. J., Antibiot. 31:539 (1978).
Martel, R. R., Can. J. Physiol. Pharmacol. 55:48 (1977).
Staruch, M. J., FASEB 3:3411 (1989).
Dumont, F. J., FASEB 3:5256 (1989).
Calne, R. Y., Lancet 1183 (1978).
Morris, R. E., Med. Sci. Res. 17:877 (1989).
Baeder, W. L., Fifth Int. Conf. Inflamm. Res. Assoc. 121 (Abstract) (1990).
Meiser, B. M., J. Heart Lung Transplant. 11 (pt. 2):197 (1992).
Stepkowski, S. M., Transplantation Proc. 23:507 (1991).

*Primary Examiner*—Robert T. Bond
*Attorney, Agent, or Firm*—Arnold S. Milowsky

[57] ABSTRACT

Compounds of the structure

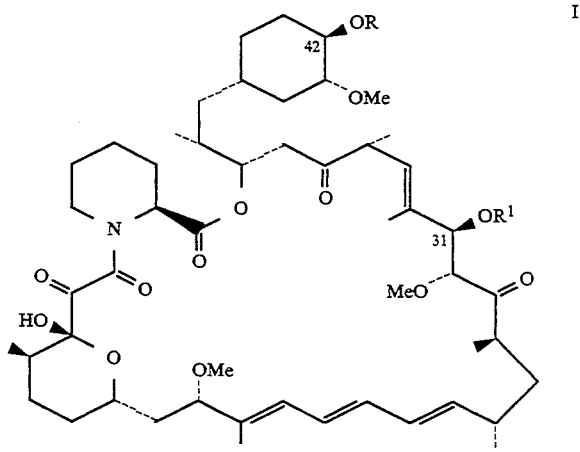

R and R¹ are each, independently, hydrogen, or (Abstract continued on next page.)

Page 2

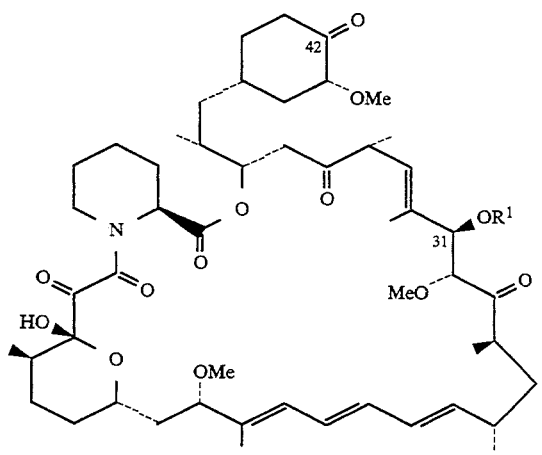

R[1] is

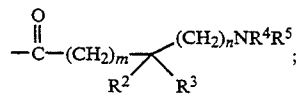

R[2] and R[3] are each, independently, hydrogen, alkyl, arylalkyl, or may be taken together to form a cycloalkyl ring;

R[4] and R[5] are each, independently, hydrogen, alkyl, arylalkyl, or may be taken together to form a saturated heterocycle wherein the heterocyclic ring may be optionally mono-, di-, or tri-substituted;

m = 0-1; and n = 0-6;

or a pharmaceutically acceptable salt thereof which are useful as immunosuppressive, antiinflammatory, antifungal, antiproliferative, and antitumor agents.

31 Claims, No Drawings

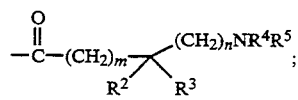

R[2] and R[3] are each, independently, alkyl, arylalkyl, or may be taken together to form a cycloalkyl ring;

R[4] and R[5] are each, independently, hydrogen, alkyl, arylalkyl, or may be taken together to form a saturated heterocycle wherein the heterocyclic ring may be optionally mono-, di-, or tri-substituted;

m = 0-1; and n = 0-6;

with the proviso that R and R[1] are not both hydrogen, or a pharmaceutically acceptable salt thereof, and

GEM-DISTRIBUTED ESTERS OF RAPAMYCIN

BACKGROUND OF THE INVENTION

This invention relates to gem-disubstituted esters of rapamycin and 42-oxorapamycin and a method for using them for inducing immunosuppression, and in the treatment of transplantation rejection, graft vs. host disease, autoimmune diseases, diseases of inflammation, adult T-cell leukemia/lymphoma, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31,539 (1978); U.S. Pat. Nos. 3,929,992; and 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], smooth muscle cell proliferation and intimal thickening following vascular injury [Morris, R. J. Heart Lung Transplant 11 (pt. 2): 197 (1992)], adult T-cell leukemia/lymphoma [European Patent Application 525,960 A1], and ocular inflammation [European Patent Application 532,862 A1].

Mono- and diacylated derivatives of rapamycin (esterified at the 28 and 43 positions) have been shown to be useful as antifungal agents (U.S. Pat. No. 4,316,885) and used to make water soluble aminoacyl prodrugs of rapamycin (U.S. Pat. No. 4,650,803). Recently, the numbering convention for rapamycin has been changed; therefore according to Chemical Abstracts nomenclature, the esters described above would be at the 31- and 42-positions.

DESCRIPTION OF THE INVENTION

This invention provides derivatives of rapamycin which are useful as immunosuppressive, antiinflammatory, antifungal, antiproliferative, and antitumor agents of Formula I having the structure

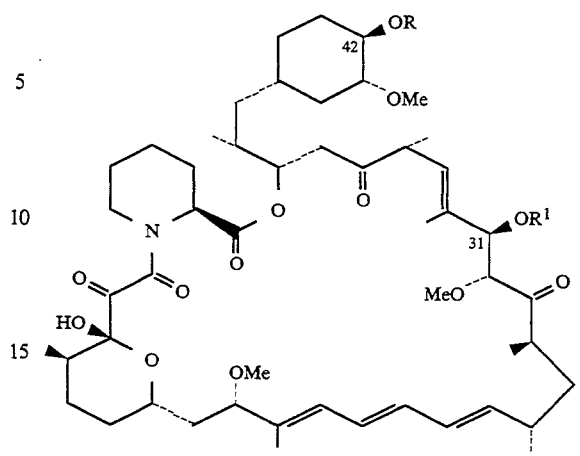

R and $R^1$ are each, independently, hydrogen, or

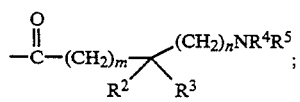

$R^2$ and $R^3$ are each, independently, alkyl of 1-6 carbon atoms, arylalkyl of 7-10 carbon atoms, or may be taken together to form a cycloalkyl ring of 3-8 carbon atoms;

$R^4$ and $R^5$ are each, independently, hydrogen, alkyl of 1-6 carbon atoms, arylalkyl of 7-10 carbon atoms, or may be taken together to form a saturated heterocycle having 3-6 carbon atoms that optionally contains an oxygen or sulfur in the heterocyclic ring, wherein the heterocyclic ring may be optionally mono-, di-, or tri-substituted with a group selected from alkyl of 1-6 carbon atoms and perfluoroalkyl of 1-6 carbon atoms;

$m = 0-1$; and
$n = 0-6$;

with the proviso that R and $R^1$ are not both hydrogen, or a pharmaceutically acceptable salt thereof.

This invention also provides derivatives of rapamycin which are useful as immunosuppressive, antiinflammatory, antifungal, antiproliferative, and antitumor agents of Formula II having the structure

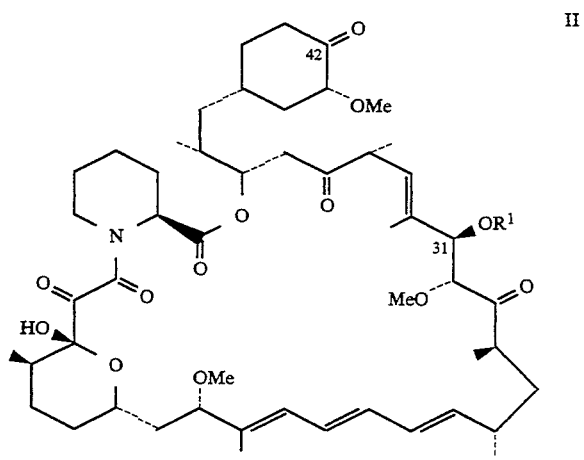

$R^1$ is

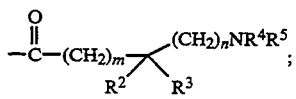

p1 $R^2$ and $R^3$ are each, independently, hydrogen, alkyl of 1–6 carbon atoms, arylalkyl of 7–10 carbon atoms, or may be taken together to form a cycloalkyl ring of 3–8 carbon atoms;

$R^4$ and $R^5$ are each, independently, hydrogen, alkyl of 1–6 carbon atoms, arylalkyl of 7–10 carbon atoms, or may be taken together to form a saturated heterocycle having 3–6 carbon atoms that optionally contains an oxygen or sulfur in the heterocyclic ring, wherein the heterocyclic ring may be optionally mono-, di-, or tri-substituted with a group selected from alkyl of 1–6 carbon atoms and perfluoroalkyl of 1–6 carbon atoms;

m=0–1; and n=0–6;

or a pharmaceutically acceptable salt thereof.

The pharmaceutically acceptable salts are those derived from such inorganic cations such as sodium, potassium, and the like; organic bases such as: mono-, di-, and trialkyl amines of 1–6 carbon atoms, per alkyl group and mono-, di-, and trihydroxyalkyl amines of 1–6 carbon atoms per alkyl group, and the like; and organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

It is preferred that the saturated heterocyclic ring as defined by $R^4$ and $R^5$ is a piperidine, morpholine, thiomorpholine, piperazine, pyrazolidine, imidazolidine, or pyrrolidine group.

It is preferred that the aryl moiety of the arylalkyl group is a phenyl, naphthyl, pyridinyl, quinolinyl, isoquinolinyl, thienyl, thionaphthyl, furanyl, benzofuranyl, benzodioxyl, benzoxazolyl, benzoisoxazolyl, indolyl, thiazolyl, isoxazolyl, pyrimidinyl, pyrazinyl, benzopyranyl, or benzimidazolyl group which may be optionally mono-, di-, or tri- substituted with a group selected from alkyl of 1–6 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, —PO$_3$H, and —CO$_2$H. It is more preferred that the aryl moiety is a phenyl group that may be optionally substituted as described above. The term alkyl of 1–6 carbon atoms includes both straight chain as well as branched carbon chains.

Of the compounds of this invention of Formula I, preferred members are those in which $R^1$ is hydrogen; those in which $R^1$ is hydrogen and m=0; those in which $R^1$ is hydrogen, m=0, and n=0; those in which $R^1$ is hydrogen, m=0, n=0, and $R^4$ and $R^5$ are hydrogen; and those in which $R^1$ is hydrogen, m=0, n=0, $R^4$ and $R^5$ are hydrogen, and $R^2$ and $R^3$ are each, independently, alkyl of 1–6 carbon atoms or cycloalkyl of 3–8 carbon atoms. Of the compounds of this invention of Formula II, preferred members include those in which m=0; those in which m=0 and $R^2$ and $R^3$ are hydrogen; and those in which m=0, $R^2$ and $R^3$ are hydrogen, and $R^4$ and $R^5$ are alkyl of 1–6 carbon atoms or may be taken together to form a saturated heterocycle having 3–6 carbon atoms that optionally contains an oxygen or sulfur in the heterocyclic ring.

Compounds that contain the ester group

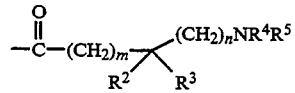

at the 42- or 31,42-positions can be prepared by activating an appropriately substituted carboxylic acid as a mixed anhydride, with an acylating group such as 2,4,6-trichlorobenzoyl chloride. Treatment of rapamycin with the mixed anhydride under mildly basic condition provides the desired compounds. Alternatively, the acylation reaction can be accomplished with 1-(3-dimethylaminopropyl)-3-ethylcarbodiimide hydrochloride and dimethylaminopyridine. Mixtures of 42- and 31,42-esters can be separated by chromatography.

The 31-ester-42-hydroxy compounds of this invention can be prepared by protecting the 42-alcohol of rapamycin with a protecting group, such as with a tert-butyl dimethylsilyl group, followed by esterification of the 31-position by the procedures described above. The preparation of rapamycin 42-silyl ethers is described in U.S. Pat. No. B1 5,120,842, which is hereby incorporated by reference. Removal of the protecting group provides the 31-esterified compounds. In the case of the tert-butyl dimethylsilyl protecting group, deprotection can be accomplished under mildly acidic conditions, such as acetic acid/water/THF. The deprotection procedure is described in Example 15 of U.S. Pat. No. 5,118,678, which is hereby incorporated by reference.

Having the 31-position esterified and the 42-position deprotected, the 42-position can be esterified using a different acylating agent than was reacted with the 31-alcohol, to give compounds having different esters at the 31- and 42-positions. Alternatively, the 42-esterified compounds, prepared as described above, can be reacted with a different acylating agent to provide compounds having different esters at the 31-and 42-positions.

Compounds that contain the ester group

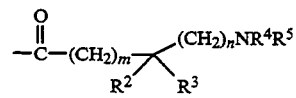

at the 31-position and a ketone at the 42-position can be prepared by first preparing 42-rapamycin from rapamycin as described in U.S. Pat. No. 5,023,263, which is hereby incorporated by reference. The 31-ester can then be prepared as described above.

This invention also covers analogous gem-disubstituted esters of other rapamycins such as, but not limited to, 29-demethoxyrapamycin, [U.S. Pat. No. 4,375,464, 32-demethoxyrapamycin under C.A. nomenclature]; rapamycin derivatives in which the double bonds in the 1-, 3-, and/or 5-positions have been reduced [U.S. Pat. No. 5,023,262]; 29-desmethylrapamycin [U.S. Pat. No. 5,093,339, 32-desmethylrapamycin under C.A. nomenclature]; 7,29-bisdesmethylrapamycin [U.S. Pat. No. 5,093,338, 7,32-desmethylrapamycin under C.A. nomenclature]; and 15-hydroxyrapamycin [U.S. Pat. No. 5,102,876]. The disclosures in the above cited U.S. Patents am hereby incorporated by reference.

Immunosuppressive activity for representative compounds of this invention was evaluated in an in vitro standard pharmacological test procedure to measure lymphocyte proliferation (LAF) and in three in vivo standard pharmacological test procedures. The pinch skin graft test procedure measures the immunosuppressive activity of the compound tested as well as the ability of the compound tested to inhibit or treat transplant rejection. The adjuvant arthritis standard pharmacological test procedure, which measures the ability of the compound tested to inhibit immune mediated inflammation. The adjuvant arthritis test procedure is a standard pharmacological test procedure for rheumatoid arthritis. Representative compounds of this invention were also evaluated in a heart allograft standard pharmacological test procedure which measures immunosuppressive activity of the compound tested as well as the ability of the compound tested to inhibit or treat transplant rejection. The procedures for these standard pharmacological test procedures are provided below.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. For each compound evaluated, rapamycin was also evaluated for the purpose of comparison. An IC$_{50}$ was obtained for each test compound as well as for rapamycin. When evaluated as a comparator for the representative compounds of this invention, rapamycin had an IC$_{50}$ ranging from 0.4–6.8 nM. The results obtained are provided as an IC$_{50}$.

Representative compounds of this invention were also evaluated in an in vivo test procedure designed to determine the survival time of pinch skin graft from male BALB/c donors transplanted to male C$_3$H(H-2K) recipients. The method is adapted from Billingham R. E. and Medawar P. B., J. Exp. Biol. 28:385–402, (1951). Briefly, a pinch skin graft from the donor was grafted on the dorsum of the recipient as a allograft, and an isograft was used as control in the same region. The recipients were treated with either varying concentrations of test compounds intraperitoneally or orally. Rapamycin was used as a test control. Untreated recipients serve as rejection control. The graft was monitored daily and observations were recorded until the graft became dry and formed a blackened scab. This was considered as the rejection day. The mean graft survival time (number of days±S.D.) of the drug treatment group was compared with the control group. The following table shows the results that were obtained. Results are expressed as the mean survival time in days. Untreated (control) pinch skin grafts are usually rejected within 6–7 days. Compounds were tested using a dose of 4 mg/kg.

The ability of the compounds of this invention to induce immunosuppression and inhibit or treat transplantation rejection was evaluated in a heterotropic heart allograft standard pharmacological test procedure that emulates transplantation rejection that occurs in humans. The following briefly describes the procedure that was used. Male BN rat neonate donors (less than 5 days of age) were humanely sacrificed, the thymus was dissected away from the heart. All connections with the thoracic cavity were severed and the heart was removed from the chest cavity and placed in cooled RPMI media where all adherent fat and fascia were removed. The heart was bisected in half, along the midline from the apex to the root of the aorta, to generate two approximately equal halves each containing atrial and ventricular tissue. Recipient male Lewis rats were anesthetized with phenobarbital (50 mg/mL; i.p.), the left inner ear was swabbed with povidine iodine, and 1 mL RPMI was injected subcutaneously above the cartilage plate to produce a fluid filled sac. A stab incision was made to the sac, into which was inserted a single half heart fragment. The pocket was sealed with a single drop of Vet-Seal (3M Animal Care Products). Recipients were divided into groups of 10 rats each. One group was untreated and the second group was treated with the compound to be treated was administered at a dosage of 300 μg/day following the transplantation procedure until graft failure occurred. Administration was i.p., either by manual injection or via an Azlet osmotic pump that was implanted into the peritoneum of the recipient rat. Grafts were inspected for loss of cardiac activity on day 7 post-transplant and subsequently on alternate days. Graft survival time is defined as the post-transplant day on which the heart graft has lost all contractile activity by visual inspection and/or cardiac monitor. Individual rejection times were averaged to produce a mean survival time for each treated group. Untreated heterotropic allografts are rejected in about 9–10 days.

The adjuvant arthritis standard pharmacological test procedure measures the ability of test compounds to prevent immune mediated inflammation and inhibit or treat rheumatoid arthritis. The following briefly describes the test procedure used. A group of rats (male inbread Wistar Lewis rats) are pre-treated with the compound to be tested (1 h prior to antigen) and then injected with Freud's Complete Adjuvant (FCA) in the right hind paw to induce arthritis. The rats are then orally dosed on a Monday, Wednesday, Friday schedule from day 0–14 for a total of 7 doses. Both hind paws are measured on days 16, 23, and 30. The difference in paw volume (mL) from day 16 to day 0 is determined and a percent change from control is obtained. The left hind paw (uninjected paw) inflammation is caused by T-cell mediated inflammation and is recorded in the above table (% change from control). The right hind paw inflammation, on the other hand, is caused by non-specific inflammation. Compounds were tested at a dose of 5 mg/kg. The results are expressed as the percent change in the uninjected paw at day 16 versus control; the more negative the percent change, the more potent the compound. Rapamycin provided between −70% and −90% change versus control, indicating that rapamycin treated rats had between 70–90% less immune induced inflammation than control rats.

The results obtained in these standard pharmacological test procedures are provided following the procedure for making the specific compounds that were tested.

The results of these standard pharmacological test procedures demonstrate immunosuppressive activity both in vitro and in vivo for the compounds of this invention. The results obtained in the LAF test procedure indicates suppression of T-cell proliferation, thereby demonstrating the immunosuppressive activity of the compounds of this invention. Further demonstration of the utility of the compounds of this invention as immunosuppressive agents was shown by the results obtained in the skin graft, adjuvant arthritis, and heart allograft standard pharmacological test procedures. Additionally, the results obtained in the skin graft and heart allograft test procedures further demonstrates the ability of the compounds of this invention to treat or inhibit transplantation rejection. The results obtained in the adjuvant arthritis standard pharmacological test procedure further demonstrate the ability of the compounds of this invention to treat or inhibit rheumatoid arthritis.

Based on the results of these standard pharmacological test procedures, the compounds are useful in the treatment or inhibition of transplantation rejection such as kidney, heart, liver, lung, bone marrow, pancreas (islet cells), cornea, small bowel, and skin allografts, and heart valve xenografts; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, and eye uveitis.

Because of the activity profile obtained, the compounds of this invention also are considered to have antitumor, antifungal activities, and antiproliferative activities. The compounds of this invention therefore also useful in treating solid tumors, adult T-cell leukemia/lymphoma, fungal infections, and hyperproliferative vascular diseases such as restenosis and atherosclerosis.

When administered for the treatment or inhibition of the above disease states, the compounds of this invention can be administered to a mammal orally, parenterally, intranasally, intrabronchially, transdermally, topically, intravaginally, or rectally.

As the compounds of Examples 5, 10, and 14 were prepared from the compounds of Examples 4, 9, and 13, respectively, the compounds of Examples 4, 9, and 13 are useful as intermediates. Additionally, a representative compound of these intermediates, Example 4, was shown to have immunosuppressive activity in the LAF and skin graft standard pharmacological test procedures. Based on these results, the compounds of Examples 4, 9, and 13 are useful in the treatment or inhibition of transplantation rejection such as kidney, heart, liver, lung, bone marrow, pancreas (islet cells), cornea, small bowel, and skin allografts, and heart valve xenografts; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, and eye uveitis. These compounds are also considered to have antitumor, antifungal activities, and antiproliferative activities. The compounds of this invention therefore also useful in treating solid tumors, adult T-cell leukemia/lymphoma, fungal infections, and hyperproliferative vascular diseases such as restenosis and atherosclerosis. When administered for the treatment or inhibition of the above disease states, the compounds of this invention can be administered to a mammal orally, parenterally, intranasally, intrabronchially, transdermally, topically, intravaginally, or rectally.

It is contemplated that when the compounds of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

The compounds of this invention can be formulated neat or with a pharmaceutical carrier to a mammal in need thereof. The pharmaceutical carrier may be solid or liquid. When formulated orally, it has been found that 0.01% Tween 80 in PHOSAL PG-50 (phospholipid concentrate with 1,2-propylene glycol, A. Nattermann & Cie. GmbH) provides an acceptable oral formulation.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carder such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carders are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 μg/kg–100 mg/kg, preferably between 0.001–25 mg/kg, and more preferably between 0.01–5 mg/kg. Treatment will generally be initiated with small dosages less than the optimum dose of the compound. Thereafter the dosage is increased until the-optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation and biological activities of representative compounds of this invention.

EXAMPLE 1

42-Oxorapamycin-31-ester with 31-N,N-dimethylglycine

To a chilled solution of 42-oxorapamycin (prepared by the procedure in U.S. Pat. No. 5,023,263) (0.212 g, 0.23 mmol) in $CH_2Cl_2$ (1.2 mL) was added dimethylglycinate (0.036 g, 0.35 mmol), 1-(3-dimethylaminopropyl)-3-ethylcarbodiimide hydrochloride (0.089 g, 0.466 mmol), and DMAP (6 mg). The reaction mixture was allowed to warm to room temperature and stirred overnight. The solution was partitioned between $CH_2Cl_2$ and water; the organic layer was separated and dried with $MgSO_4$. Flash chromatography (0–50% acetone/ethyl acetate) yielded 0.117 g (0.117 mmol, 51%) of the title compound as a white solid. Negative FAB-MS [M-H]−@m/z996.

Results obtained in standard pharmacological test procedures: LAFIC$_{50}$: 9.7 nM Skin graft survival time: 9.6±0.9 days

EXAMPLE 2

42-Oxorapamycin-31-ester with 31-N,N-dimethylglycine hydrochloride salt

To a chilled (ice bath) solution of 42-oxorapamycin-31-ester with 31-N,N-dimethylglycine (0.199 g, 0.2 mmol) in anhydrous ether (5 mL) was added dropwise via syringe 0.20 mL 1N HCl/ether. A white precipitate formed immediately. The reaction mixture was allowed to stand for 15 min, filtered, and dried in vacuo to yield 0.159 g (0.154 mmol, 77%) of the title compound as an off-white solid. Negative FAB-MS [M-H]−@m/z996 (free base).

Results obtained in standard pharmacological test procedures: LAF IC$_{50}$: 23.4 nM Skin graft survival time: 10.0±0.0 days and 10.3±0.5 days

EXAMPLE 3

42-Oxorapamycin-31-ester with 31-N,N-dimethylglycine maleate salt

To a chilled (ice bath) solution of 42-oxorapamycin-31-ester with 31-N,N-dimethylglycine (0.187 g, 0.188 mmol) in anhydrous ether (8 mL) was added dropwise via syringe 0.022 g (0.19 mmol) of maleic acid in 1.0 mL of ether. A white precipitate formed immediately. The reaction mixture was allowed to stand for 15 min, filtered, and dried in vacuo to yield 0.129 g (0.12 mmol, 63%) of the title compound as a white solid. Negative FAB-MS [M-H]−@m/z 996 (free base).

Results obtained in standard pharmacological test procedures: LAF IC$_{50}$: 14.4 nM Skin graft survival time: 9.2±1.3 days

EXAMPLE 4

Rapamycin 42-ester with 2-(9H-fluoren-9-ylmethoxycarbonylamino)-2-methylpropionic acid To a chilled solution of 2-(9H-fluoren-9-ylmethoxycarbonylamino)-2-methylpropionic acid (0.3 g, 0.922 mmol) in 3 mL of THF was added triethylamine (0.19 mL, 1.36 mmol) and trichlorobenzoyl chloride (0.22 mL, 1.4 mmol). The entire above solution was added to a chilled solution of rapamycin (0.84 g, 0.92 mmol) in 2 mL of THF. DMAP (0.11 g, 0.9 mmol) was added and the reaction mixture was allowed to warm to room temperature and stirred overnight. The mixture was filtered, the filtrate was concentrated to ¼ volume, and an excess of ethyl acetate was added. The ethyl acetate layer was washed with 0.5N HCl, saturated sodium bicarbonate, and brine; it was then dried and concentrated in vacuo to yield 1.3 g (>100%) of a light yellow foam. Flash chromatography (25–50% EtOAc/hexane, then 50% EtOAc/hexane) yielded 0.070 g (0.057 mmol, 6.4%) of the title compound as a white solid. Negative FAB-MS [M-H]⁻@m/z 1220.

Results obtained in standard pharmacological test procedures: LAF IC$_{50}$: 6.6 and 2.5 nM Skin graft survival time: 11.7±0.8 and 14.2±0.6 days

EXAMPLE 5

Rapamycin 42-ester with 2-amino-2-methylpropionic acid

To a chilled (ice bath) solution of rapamycin 42-ester with 2-(9H-fluoren-9-ylmethoxycarbonylamino)-2-methylpropionic acid (2.09 g, 1.71 mmol) in acetonitrile (10 mL) was added 1 mL of piperidine in 4 mL of acetonitrile via an addition funnel. The reaction mixture was stirred at 0.5° C. for one hour, at which time a white precipitate formed. The reaction mixture was filtered, concentrated in vacuo (without heating), and immediately applied to a flash chromatography column. Flash chromatography (2×; 3% methanol/chloroform, then 2% MeOH/CHCl$_3$) yielded 0.735 g (0.736 mmol, 43%) of the title compound as an off-white solid. Negative FAB-MS [M-H]⁻@m/z 998.

Results obtained in standard pharmacological test procedures: LAF IC$_{50}$: 7.0 and 3.21 nM Skin graft survival time: 12.3±1.0 and 11.8±1.3 days

EXAMPLE 6

Rapamycin 42-ester with 2-amino-2-methylpropionic acid maleate salt

To a chilled (ice bath) solution of rapamycin 42-ester with 2-amino-2-methylpropionic acid (0.258 g, 0.258 mmol) in anhydrous ether (5 mL) was added dropwise via syringe 0.030 g (0.258 mmol) of maleic acid in 1.5 mL of ether. A white precipitate formed immediately. The reaction mixture was allowed to stand for 15 min, filtered, and dried in vacuo to yield 0.204 g (0.183 mmol, 71%) of the title compound as a white solid. Negative FAB-MS [M-H]⁻@m/z 998 (free base).

Results obtained in standard pharmacological test procedures: LAF IC$_{50}$: 5.3 and 8.4 nM Skin graft survival time: 12.0±0.0 and 11.0±0.9 days Percent change in adjuvant arthritis versus control: −73% Heart allograft survival time: 19.11 days

EXAMPLE 7

Rapamycin 42-ester with 2-amino-2,-methylpropionic acid hydrochloride salt

To a chilled (ice bath) solution of rapamycin 42-ester with 2-amino-2-methylpropionic acid (0.295 g, 0.295 mmol) in anhydrous ether (5 mL) was added dropwise via syringe 0.30 mL 1N HCl/ether. A white precipitate formed immediately. The reaction mixture was allowed to stand for 15 min, filtered, and dried in vacuo to yield 0.207 g (0.2 mmol, 68%) of product as an off-white solid. Negative FAB-MS [M-H]⁻@m/z 998 (free base).

Results obtained in standard pharmacological test procedures: LAF IC$_{50}$: 3.9 nM Skin graft survival time: 10.2±1.2 days

EXAMPLE 8

1-(9H-Fluoren-9-ylmethoxycarbonylamino)-cyclopentane carboxylic acid

To a chilled (ice bath) suspension of aminocyclopentanecarboxylic acid (1.05 g, 8.13 mmol) in alumina-filtered dioxane (8 mL) was added 10% Na$_2$CO$_3$ (16.5 mL). The reaction mixture became clearer (but not completely clear) after 10% Na$_2$CO$_3$ was added. A solution of a fluorenylmethyl chloroformate (2.11 g, 8.16 mmol in 12 mL dioxane) was then slowly added to the reaction mixture, which became (and remained) cloudy. The reaction mixture was allowed to warm to room temperature (∼20° C.) and was stirred overnight under N$_2$. The reaction mixture was poured into ice water (∼150 mL) and extracted three times with anhydrous ether. (Some product went into the ether layer). The aqueous layer was chilled in an ice bath, acidified with concentrated HCl to pH of about 2, and extracted three times with ethyl acetate (3×50 mL). The combined ethyl acetate layers were washed with 0.1N HCl and H$_2$O. The ether and ethyl acetate layers were dried over MgSO$_4$, combined and concentrated. Flash chromatography (40–50% ethyl acetate/hexane) gave the title compound as a white foam in a yield of 16.6% (0.476 g (1.35 mmol). DEI m+@m/z 351.

EXAMPLE 9

Rapamycin 42-ester with 1-(9H-fluoren-9-ylmethoxycarbonylamino)-cyclopentane carboxylic acid To a stirred solution of (9H-fluoren-9-ylmethoxycarbonylamino)-cyclopentane carboxylic acid (0.9926 g, 2.82 mmol) in anhydrous THF (8 mL) were added diisopropylethylamine (0.49 mL, 2.82 mmol) in THF (5 mL) and trichlorobenzoyl chloride (0.37 mL, 2.73 mmol) in THF (4 mL). The reaction mixture was stirred 2.5 hours at room temperature. Rapamycin (2.17 g, 2.37 mmol) in THF (8 mL) and DMAP (0.350 g, 2.86 mmol) were then added to the reaction mixture, which was allowed to stir overnight at room temperature. It was then concentrated, partitioned in methylene chloride/water, and washed with 0. 1N HCl and water. The organic layer was dried over anhydrous MgSO$_4$, filtered and concentrated. The resulting foam was flash chromatographed with a gradient of 25–50% EtOAc/hexane to yield the title compound as white foam (0.883 g, 0.708 mmol) in 29.8% yield. Negative FAB-MS [M-H]⁻@m/z 1246.

EXAMPLE 10

Rapamycin 42-ester with 1-aminocyclopentane carboxylic acid

To a chilled (ice bath) solution of rapamycin 42-ester with 1-(9H-fluoren-9-ylmethoxycarbonylamino)-cyclopentane carboxylic acid (0.991 g, 0.794 mmol) in acetonitrile (4.5 mL) was added 0.47 mL (4.76 mmol) of piperidine in 2 mL of acetonitrile via an additional funnel. The reaction mixture was stirred at 0-5° C. for about two hours (a white precipitate formed after an hour). The reaction mixture was then filtered and concentrated (without heating) and applied to a flash column with a gradient of 1–1.5% methanol/chloroform to yield 0.36 g (0.35 mmole, 44%) of the title compound. Negative FAB-MS [M-H]⁻@m/z 1024.

Results obtained in standard pharmacological test procedures: LAF IC$_{50}$: 6.0 nM Skin graft survival time: 10.5±0.6 and 10.2±1.0 days

EXAMPLE 11

Rapamycin 42-ester with 1-aminocyclopentane carboxylic acid hydrochloride salt

To a chilled (ice bath) solution of rapamycin 42-ester with 1-aminocyclopentane carboxylic acid (0.220 g 0.214 mmol) in anhydrous ethyl ether (4 mL) (N$_2$ atmosphere) was added 0.22 mL (0.22 mmol) of 1N HCl/ether dropwise via syringe. A light yellow precipitate formed immediately. The reaction mixture was allowed to sit for 10 minutes under nitrogen. It was then filtered and the pale yellow solid was dried on vacuum pump to yield 0.131 g (0.124 mmol, 57.7% yield) of the title compound. Negative FAB-MS [M-H]⁻@m/z 1024.

Results obtained in standard pharmacological test procedures: LAF IC$_{50}$: 0.63 nM Skin graft survival time: 10.3±0.5, 11.5±0.8, and 12.3±1.0 days

EXAMPLE 12

1-(9H-Fluoren-9-ylmethoxycarbonylamino)-cyclohexane carboxylic acid

To a chilled (ice bath) suspension of aminocyclohexanecarboxylic acid (2.51 g, 17.5 mmol) in alumina-filtered dioxane (17 mL) were added 10% Na$_2$CO$_3$ (35 mL) and a solution of 9-fluorenylmethylchloroformate (4.57 g, 17.7 mmol) in 26 mL of dioxane (added slowly). The reaction mixture was allowed to warm to about 20° C. and stirred overnight under N$_2$. The reaction mixture was poured into ~300 mL of ice water and washed with anhydrous ether (some product went into the ether layer). The aqueous layer was chilled in an ice bath and acidified with concentrated hydrochloric acid to pH about 2. The aqueous layer was then extracted with ethyl acetate (3×100 mL). The combined ethyl acetate layers were washed with 0.1N HCl and H$_2$O. The ether and ethyl acetate layers were dried over anhydrous MgSO$_4$, combined and concentrated. The resulting compound was flash chromatographed with a gradient of 40–50% EtOAc/Hexane to yield 0.383 g (1.05 mmol, 6.0% yield) of the title compound as a white foam DEI M+@m/z=365.

EXAMPLE 13

Rapamycin 42-ester with 1-(9H-fluoren-9-ylmethoxycarbonylamino)-cyclohexane carboxylic acid To a stirred solution of 1-(9H-fluoren-9-ylmethoxycarbonylamino)-cyclohexane carboxylic acid (1.24 g, 3.39 mmol) in 9 mL of anhydrous THF were added diisopropylethylamine (0.59 mL, 3.4 mmol) in 6 mL THF and trichlorobenzoylchloride (0.51 mL, 3.28 mmol) in 4 mL THF. The clear reaction mixture was stirred for 2½ hours, at which time rapamycin (2.63 g, 2.88 mmol) in 9 mL THF and DMAP (0.423 g, 3.46 mmol) were added. The solution was then stirred overnight at room temperature. The reaction mixture was concentrated and partitioned in methylene chloride/water. The organic layer was washed with 0.1N HCl and water. The organic layer was dried, concentrated, and flash chromatographed with a gradient of 30–40% ethyl acetate/hexane to give 1.3 g of an off-white foam. It was then chromatographed on a normal phase Rainin HPLC column with a flow rate of 40 mL/min and a solvent system of 50% ethyl acetate/hexane to yield 1.03 g (0.816 mmol, 28.4% yield) of the title compound as a white foam Negative FAB-MS [M-H]⁻@m/z 1260.

EXAMPLE 14

Rapamycin 42-ester with 1-aminocyclohexane carboxylic acid

To a chilled (ice bath) solution of rapamycin 42-ester with 1-(9H-fluoren-9-ylmethoxycarbonylamino)-cyclohexane carboxylic acid (1.01 g, 0.800 mmol) in acetonitrile (4.5 mL) was added piperidine (0.48 mL, 4.9 mmole via addition funnel) dropwise in 2 mL THF. The reaction mixture was stirred about two hours. The precipitate which had formed was filtered, and the filtrate was concentrated (without heat) and immediately flash chromatographed (1% methanol/chloroform) to yield the title compound as an off white foam (0.428 g, 0.412 mmol, 51.6% yield). Negative FAB-MS [M-H]⁻@m/z 1038.

Results obtained in standard pharmacological test procedures: LAF IC$_{50}$: 1.7 and 0.7 nM Skin graft survival time: 10.6±0.5 and 12.4±1.1 days

EXAMPLE 15

Rapamycin 42-ester with 1-aminocyclohexane carboxylic acid hydrochloride salt

To a chilled (ice bath) solution of rapamycin 42-ester with 1-aminocyclohexane carboxylic acid (0.211 g, 0.204 mmol) under N$_2$ in anhydrous ether (4 mL) was added 1N HCl ether (0.22 mL, 0.22 mmol). A pale yellow precipitate formed immediately. The reaction mixture was allowed to sit for ~10 min. Filtration yielded a pale yellow solid which was dried on the vacuum pump to yield 0.065 g (0.061 mmol, 29.7% yield) of the title compound. Negative FAB-MS [M-H]⁻@m/z 1038.

Results obtained in standard pharmacological test procedures: LAF IC$_{50}$: 0.7 and 0.4 nM Skin graft survival time: 11.5±1.2 and 11.2±0.8 days

What is claimed is:

1. A compound of the structure

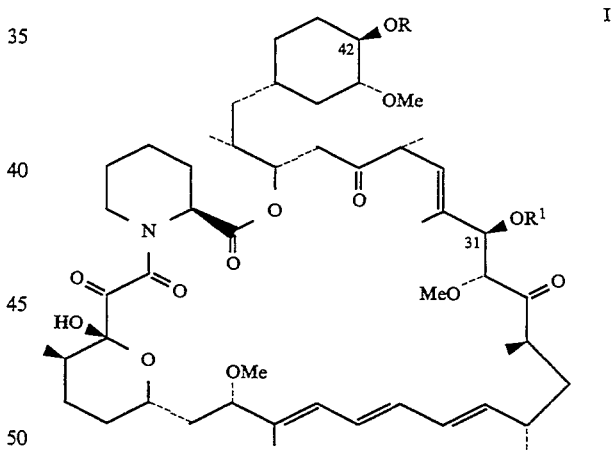

R and R¹ are each, independently, hydrogen, or

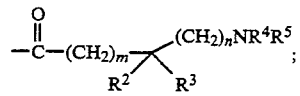

R² and R³ are each, independently, alkyl of 1–6 carbon atoms, arylalkyl of 7–10 carbon atoms, or may be taken together to form a cycloalkyl ring of 3–8 carbon atoms;

R⁴ and R⁵ are each, independently, hydrogen, alkyl of 1–6 carbon atoms, arylalkyl of 7–10 carbon atoms, or may be taken together to form a saturated heterocycle having 3–6 carbon atoms selected from the group consisting of piperidine, morpholine, thiomorpholine, piperazine, pyrazolidine, imidazolidine, and pyrrolidine, wherein the heterocyclic ring may be optionally mono-, di-, or tri-substituted with a group selected from alkyl of 1–6 carbon atoms and perfluoroalkyl of 1–6 carbon atoms;

wherein the aryl moiety of the arylalkyl group of $R^2$, $R^3$, $R^4$, and $R^5$ is a phenyl, naphthyl, pyridinyl, quionlinyl, isoquinolinyl, thienyl, thionaphthyl, furanyl, benzofuranyl, benzodioxyl, benzoxazolyl, benzoisoxazolyl, indolyl, thiazolyl, isoxazolyl, pyrimidinyl, pyrazinyl, benzopyranyl, or benzimidazolyl group which may be optionally mono-, di-, or tri-substituted with a group selected from alkyl of 1–6 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —$SO_3H$, —$PO_3H$, and —$CO_2H$;

$m = 0–1$; and $n = 0–6$;

with the proviso that R and $R^1$ are not both hydrogen, or a pharmaceutically acceptable salt thereof.

2. The compound of claim 1 wherein $R^1$ is hydrogen or a pharmaceutically acceptable salt thereof.

3. The compound of claim 2 wherein $m = 0$ or a pharmaceutically acceptable salt thereof.

4. The compound according to claim 3 wherein $n = 0$ or a pharmaceutically acceptable salt thereof.

5. The compound according to claim 4 wherein $R^4$ and $R^5$ are hydrogen or a pharmaceutically acceptable salt thereof.

6. The compound according to claim 5 wherein $R^2$ and $R^3$ are each, independently, alkyl of 1–6 carbon atoms or cycloalkyl of 3–8 carbon atoms or a pharmaceutically acceptable salt thereof.

7. The compound according to claim 1 which is Rapamycin 42-ester with 2-amino-2-methylpropionic acid or a pharmaceutically acceptable salt thereof.

8. The compound according to claim 1 which is rapamycin 42-ester with 2-amino-2-methylpropionic acid maleate salt.

9. The compound according to claim 1 which is rapamycin 42-ester with 2-amino-2-methylpropionic acid hydrochloride salt.

10. The compound according to claim 1 which is rapamycin 42-ester with 1-aminocyclopentane carboxylic acid or a pharmaceutically acceptable salt thereof.

11. The compound according to claim 1 which is rapamycin 42-ester with 1-aminocyclopentane carboxylic acid hydrochloride salt.

12. The compound according to claim 1 which is rapamycin 42-ester with 1-aminocyclohexane carboxylic acid or a pharmaceutically acceptable salt thereof.

13. The compound according to claim 1 which is rapamycin 42-ester with 1-aminocyclohexane carboxylic acid hydrochloride salt.

14. A compound of the structure

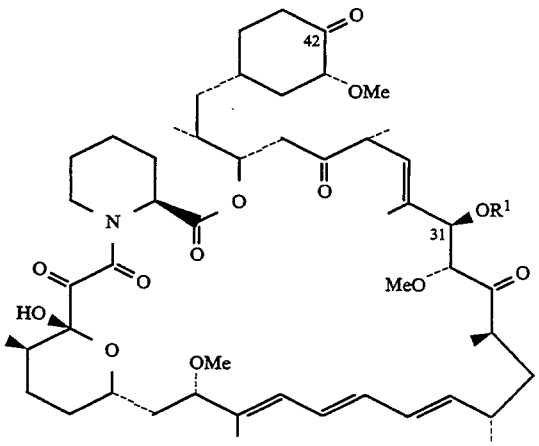

$R^1$ is

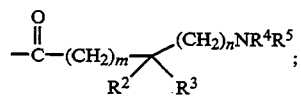

$R^2$ and $R^3$ are each, independently, alkyl of 1–6 carbon atoms, arylalkyl of 7–10 carbon atoms, or may be taken together to form a cycloalkyl ring of 3–8 carbon atoms;

$R^4$ and $R^5$ are each, independently, hydrogen, alkyl of 1–6 carbon atoms, arylalkyl of 7–10 carbon atoms, or may be taken together to form a saturated heterocycle having 3–6 carbon atoms selected from the group consisting of piperidine, morpholine, thiomorpholine, piperazine, pyrazolidine, imidazolidine, and pyrrolidine, wherein the heterocyclic ring may be optionally mono-, di-, or tri-substituted with a group selected from alkyl of 1–6 carbon atoms and perfluoroalkyl of 1–6 carbon atoms;

wherein the aryl moiety of the arylalkyl group of $R^2$, $R^3$, $R^4$, and $R^5$ is a phenyl, naphthyl, pyridinyl, quionlinyl, isoquinolinyl, thienyl, thionaphthyl, furanyl, benzofuranyl, benzodioxyl, benzoxazolyl, benzoisoxazolyl, indolyl, thiazolyl, isoxazolyl, pyrimidinyl, pyrazinyl, benzopyranyl, or benzimidazolyl group which may be optionally mono-, di-, or tri-substituted with a group selected from alkyl of 1–6 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —$SO_3H$, —$PO_3H$, and —$CO_2H$;

$m = 0–1$; and $n = 0–6$;

or a pharmaceutically acceptable salt thereof.

15. A compound of claim 13 wherein $m = 0$ or a pharmaceutically acceptable salt thereof.

16. A compound of claim 14 wherein $R^2$ and $R^3$ are hydrogen or a pharmaceutically acceptable salt thereof.

17. A compound of claim 15 wherein $R^4$ and $R^5$ are alkyl of 1–6 carbon atoms or may be taken together to form a saturated heterocycle having 3–6 carbon atoms that optionally contains an oxygen or sulfur in the heterocyclic ring or a pharmaceutically acceptable salt thereof.

18. A compound of claim 13 which is 42-oxorapamycin-31-ester with 31-N,N-dimethylglycine or a pharmaceutically acceptable salt thereof.

19. A compound of claim 13 which is 42-oxorapamycin-31-ester with 31-N,N-dimethylglycine hydrochloride salt.

20. A compound of claim 13 which is 42-oxorapamycin-31-ester with 31-N,N-dimethylglycine maleate salt.

21. A method of inducing immunosuppression of a mammal in need thereof, which comprises administering an immunosuppressive effective amount of a compound of the structure

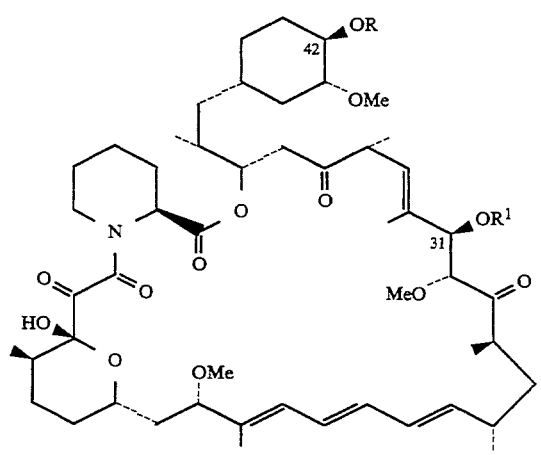

R and $R^1$ are each, independently, hydrogen, or

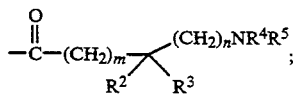

$R^2$ and $R^3$ are each, independently, alkyl of 1–6 carbon atoms, arylalkyl of 7–10 carbon atoms, or may be taken together to form a cycloalkyl ring of 3–8 carbon atoms;

$R^4$ and $R^5$ are each, independently, hydrogen, alkyl of 1–6 carbon atoms, arylalkyl of 7–10 carbon atoms, or may be taken together to form a saturated heterocycle having 3–6 carbon atoms selected from the group consisting of piperidine, morpholine, thiomorpholine, piperazine, pyrazolidine, imidazolidine, and pyrrolidine, wherein the heterocyclic ring may be optionally mono-, di-, or tri-substituted with a group selected from alkyl of 1–6 carbon atoms and perfluoroalkyl of 1–6 carbon atoms;

wherein the aryl moiety of the arylalkyl group of $R^2$, $R^3$, $R^4$, and $R^5$ is a phenyl, naphthyl, pyridinyl, quionlinyl, isoquinolinyl, thienyl, thionaphthyl, furanyl, benzofuranyl, benzodioxyl, benzoxazolyl, benzoisoxazolyl, indolyl, thiazolyl, isoxazolyl, pyrimidinyl, pyrazinyl, benzopyranyl, or benzimidazolyl group which may be optionally mono-, di-, or tri-substituted with a group selected from alkyl of 1–6 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, —PO$_3$H, and —CO$_2$H;

m = 0–1; and
n = 0–6;

with the proviso that R and $R^1$ are not both hydrogen, or a pharmaceutically acceptable salt thereof.

22. A method of inducing immunosuppression in a mammal in need thereof, which comprises administering an immunosuppressive effective amount of a compound of the structure

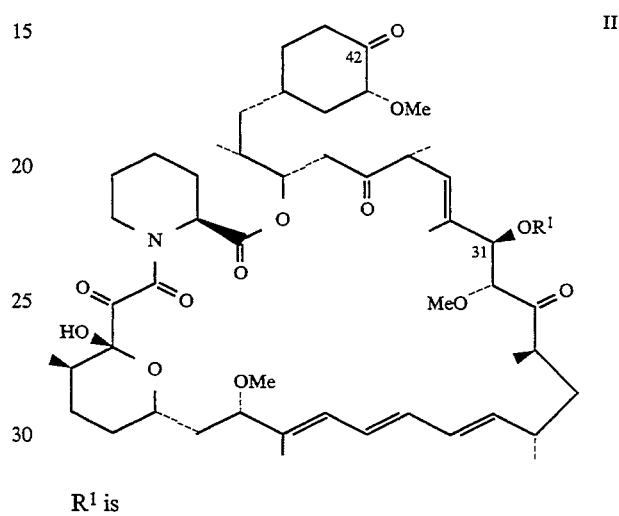

$R^1$ is

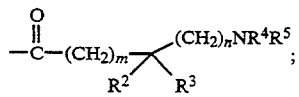

$R^2$ and $R^3$ are each, independently, hydrogen, alkyl of 1–6 carbon atoms, arylalkyl of 7–10 carbon atoms, or may be taken together to form a cycloalkyl ring of 3–8 carbon atoms;

$R^4$ and $R^5$ are each, independently, hydrogen, alkyl of 1–6 carbon atoms, arylalkyl of 7–10 carbon atoms, or may be taken together to form a saturated heterocycle having 3–6 carbon atoms selected from the group consisting of piperidine, morpholine, thiomorpholine, piperazine, pyrazolidine, imidazolidine, and pyrrolidine, wherein the heterocyclic ring may be optionally mono-, di-, or tri-substituted with a group selected from alkyl of 1–6 carbon atoms and perfluoroalkyl of 1–6 carbon atoms;

wherein the aryl moiety of the arylalkyl group of $R^2$, $R^3$, $R^4$, and $R^5$ is a phenyl, naphthyl, pyridinyl, quionlinyl, isoquinolinyl, thienyl, thionaphthyl, furanyl, benzofuranyl, benzodioxyl, benzoxazolyl, benzoisoxazolyl, indolyl, thiazolyl, isoxazolyl, pyrimidinyl, pyrazinyl, benzopyranyl, or benzimidazolyl group which may be optionally mono-, di-, or tri-substituted with a group selected from alkyl of 1–6 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, —PO$_3$H, and —CO$_2$H;

m=0–1; and n=0–6;

or a pharmaceutically acceptable salt thereof.

23. A method of treating transplantation rejection or graft vs. host disease in a mammal in need thereof which comprises administering an antirejection effective amount of a compound of the structure

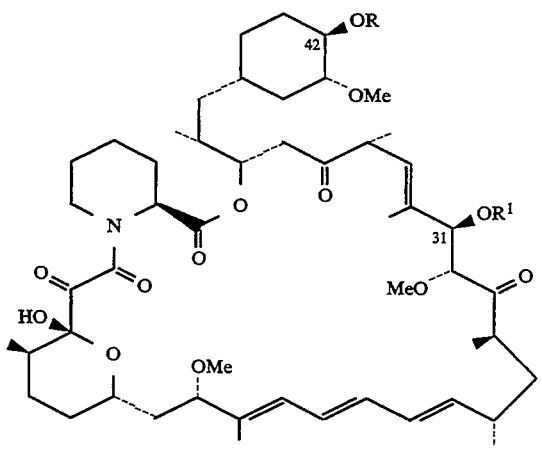

I

R and R$^1$ are each, independently, hydrogen, or

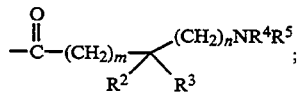

R$^2$ and R$^3$ are each, independently, alkyl of 1–6 carbon atoms, arylalkyl of 7–10 carbon atoms, or may be taken together to form a cycloalkyl ring of 3–8 carbon atoms;

R$^4$ and R$^5$ are each, independently, hydrogen, alkyl of 1–6 carbon atoms, arylalkyl of 7–10 carbon atoms, or may be taken together to form a saturated heterocycle having 3–6 carbon atoms selected from the group consisting of piperidine, morpholine, thiomorpholine, piperazine, pyrazolidine, imidazolidine, and pyrrolidine, wherein the heterocyclic ring may be optionally mono-, di-, or tri-substituted with a group selected from alkyl of 1–6 carbon atoms and perfluoroalkyl of 1–6 carbon atoms;

wherein the aryl moiety of the arylalkyl group of R$^2$, R$^3$, R$^4$, and R$^5$ is a phenyl, naphthyl, pyridinyl, quionlinyl, isoquinolinyl, thienyl, thionaphthyl, furanyl, benzofuranyl, benzodioxyl, benzoxazolyl, benzoisoxazolyl, indolyl, thiazolyl, isoxazolyl, pyrimidinyl, pyrazinyl, benzopyranyl, or benzimidazolyl group which may be optionally mono-, di-, or tri-substituted with a group selected from alkyl of 1–6 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, —PO$_3$H, and —CO$_2$H;

m=0–1; and n=0–6;

with the proviso that R and R$^1$ are not both hydrogen, or a pharmaceutically acceptable salt thereof.

24. A method of treating transplantation rejection or graft vs. host disease in a mammal in need thereof which comprises administering an antirejection effective amount of a compound of the structure

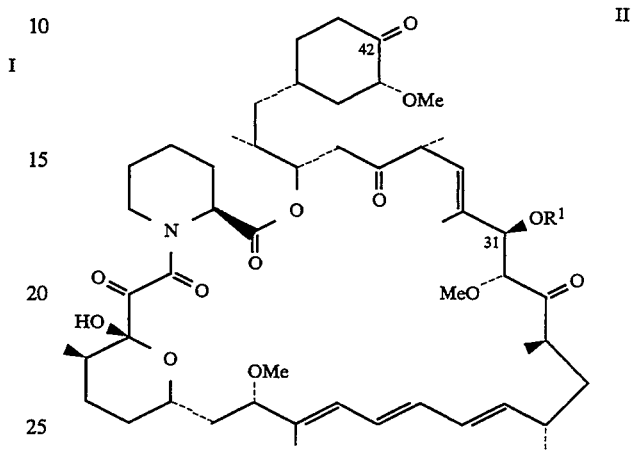

II

R$^1$ is

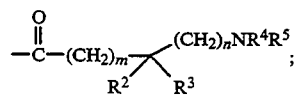

R$^2$ and R$^3$ are each, independently, hydrogen, alkyl of 1–6 carbon atoms, arylalkyl of 7–10 carbon atoms, or may be taken together to form a cycloalkyl ring of 3–8 carbon atoms;

R$^4$ and R$^5$ are each, independently, hydrogen, alkyl of 1–6 carbon atoms, arylalkyl of 7–10 carbon atoms, or may be taken together to form a saturated heterocycle having 3–6 carbon atoms selected from the group consisting of piperidine, morpholine, thiomorpholine, piperazine, pyrazolidine, imidazolidine, and pyrrolidine, wherein the heterocyclic ring may be optionally mono-, di-, or tri-substituted with a group selected from alkyl of 1–6 carbon atoms and perfluoroalkyl of 1–6 carbon atoms;

wherein the aryl moiety of the arylalkyl group of R$^2$, R$^3$, R$^4$, and R$^5$ is a phenyl, naphthyl, pyridinyl, quionlinyl, isoquinolinyl, thienyl, thionaphthyl, furanyl, benzofuranyl, benzodioxyl, benzoxazolyl, benzoisoxazolyl, indolyl, thiazolyl, isoxazolyl, pyrimidinyl, pyrazinyl, benzopyranyl, or benzimidazolyl group which may be optionally mono-, di-, or tri-substituted with a group selected from alkyl of 1–6 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, —PO$_3$H, and —CO$_2$H;

m=0–1; and n=0–6;

or a pharmaceutically acceptable salt thereof

25. A method of treating rheumatoid arthritis in mammal in need thereof which comprises administering an antiarthritis effective amount of a compound of the structure

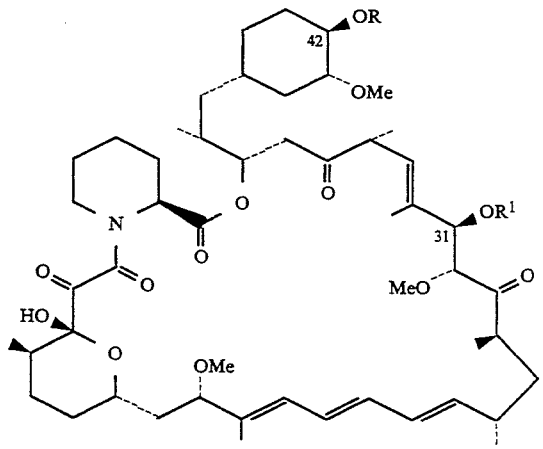   I

R and $R^1$ are each, independently, hydrogen, or

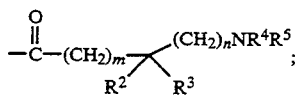

$R^2$ and $R^3$ are each, independently, alkyl of 1-6 carbon atoms, arylalkyl of 7-10 carbon atoms, or may be taken together to form a cycloalkyl ring of 3-8 carbon atoms;

$R^4$ and $R^5$ are each, independently, hydrogen, alkyl of 1-6 carbon atoms, arylalkyl of 7-10 carbon atoms, or may be taken together to form a saturated heterocycle having 3-6 carbon atoms selected from the group consisting of piperidine, morpholine, thiomorpholine, piperazine, pyrazolidine, imidazolidine, and pyrrolidine, wherein the heterocyclic ring may be optionally mono-, di-, or tri-substituted with a group selected from alkyl of 1-6 carbon atoms and perfluoroalkyl of 1-6 carbon atoms;

wherein the aryl moiety of the arylalkyl group of $R^2$, $R^3$, $R^4$, and $R^5$ is a phenyl, naphthyl, pyridinyl, quionlinyl, isoquinolinyl, thienyl, thionaphthyl, furanyl, benzofuranyl, benzodioxyl, benzoxazolyl, benzoisoxazolyl, indolyl, thiazolyl, isoxazolyl, pyrimidinyl, pyrazinyl, benzopyranyl, or benzimidazolyl group which may be optionally mono-, di-, or tri-substituted with a group selected from alkyl of 1-6 carbon atoms, alkoxy of 1-6 carbon atoms, cyano, halo, hydroxy, nitro, carbalkoxy of 2-7 carbon atoms, trifluoromethyl, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, alkylthio of 1-6 carbon atoms, —$SO_3H$, —$PO_3H$, and —$CO_2H$;

m=0-1; and
n=0-6;

with the proviso that R and $R^1$ are not both hydrogen, or a pharmaceutically acceptable salt thereof.

26. A method of treating rheumatoid arthritis in mammal in need thereof which comprises administering an antiarthritis effective amount of a compound of the structure

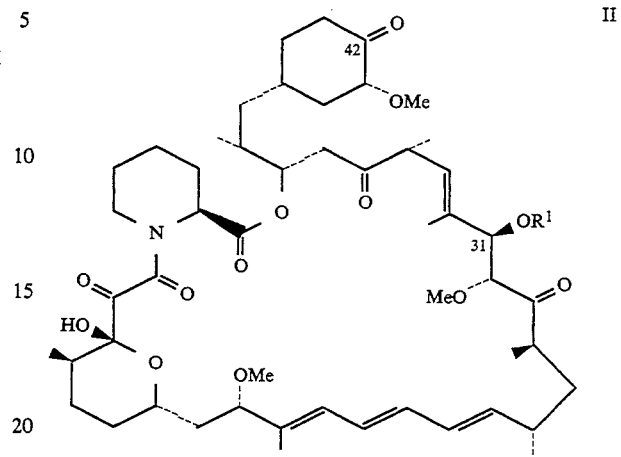   II $R^1$ is

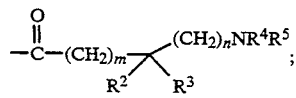

$R^2$ and $R^3$ are each, independently, hydrogen, alkyl of 1-6 carbon atoms, arylalkyl of 7-10 carbon atoms, or may be taken together to form a cycloalkyl ring of 3-8 carbon atoms;

$R^4$ and $R^5$ are each, independently, hydrogen, alkyl of 1-6 carbon atoms, arylalkyl of 7-10 carbon atoms, or may be taken together to form a saturated heterocycle having 3-6 carbon atoms selected from the group consisting of piperidine, morpholine, thiomorpholine, piperazine, pyrazolidine, imidazolidine, and pyrrolidine, wherein the heterocyclic ring may be optionally mono-, di-, or tri-substituted with a group selected from alkyl of 1-6 carbon atoms and perfluoroalkyl of 1-6 carbon atoms;

wherein the aryl moiety of the arylalkyl group of $R^2$, $R^3$, $R^4$, and $R^5$ is a phenyl, naphthyl, pyridinyl, quionlinyl, isoquinolinyl, thienyl, thionaphthyl, furanyl, benzofuranyl, benzodioxyl, benzoxazolyl, benzoisoxazolyl, indolyl, thiazolyl, isoxazolyl, pyrimidinyl, pyrazinyl, benzopyranyl, or benzimidazolyl group which may be optionally mono-, di-, or tri-substituted with a group selected from alkyl of 1-6 carbon atoms, alkoxy of 1-6 carbon atoms, cyano, halo, hydroxy, nitro, carbalkoxy of 2-7 carbon atoms, trifluoromethyl, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, alkylthio of 1-6 carbon atoms, —$SO_3H$, —$PO_3H$, and —$CO_2H$;

m=0-1; and
n=0-6;

or a pharmaceutically acceptable salt thereof.

27. A pharmaceutical composition which comprises a compound of the structure

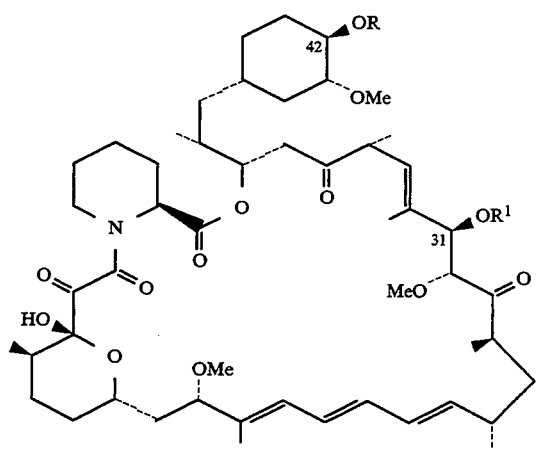

R and R¹ are each, independently, hydrogen, or

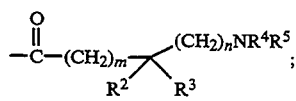

R² and R³ are each, independently, alkyl of 1–6 carbon atoms, arylalkyl of 7–10 carbon atoms, or may be taken together to form a cycloalkyl ring of 3–8 carbon atoms;

R⁴ and R⁵ are each, independently, hydrogen, alkyl of 1–6 carbon atoms, arylalkyl of 7–10 carbon atoms, or may be taken together to form a saturated heterocycle having 3–6 carbon atoms selected from the group consisting of piperidine, morpholine, thiomorpholine, piperazine, pyrazolidine, imidazolidine, and pyrrolidine, wherein the heterocyclic ring may be optionally mono-, di-, or tri-substituted with a group selected from alkyl of 1–6 carbon atoms and perfluoroalkyl of 1–6 carbon atoms;

wherein the aryl moiety of the arylalkyl group of R², R³, R⁴, and R⁵ is a phenyl, naphthyl, pyridinyl, quionlinyl, isoquinolinyl, thienyl, thionaphthyl, furanyl, benzofuranyl, benzodioxyl, benzoxazolyl, benzoisoxazolyl, indolyl, thiazolyl, isoxazolyl, pyrimidinyl, pyrazinyl, benzopyranyl, or benzimidazolyl group which may be optionally mono-, di-, or tri-substituted with a group selected from alkyl of 1–6 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO₃H, —PO₃H, and —CO₂H;

m=0–1; and
n=0–6;

with the proviso that R and R¹ are not both hydrogen, or a pharmaceutically acceptable salt thereof, and a pharmaceutical carrier.

28. A pharmaceutical composition which comprises a compound of the structure

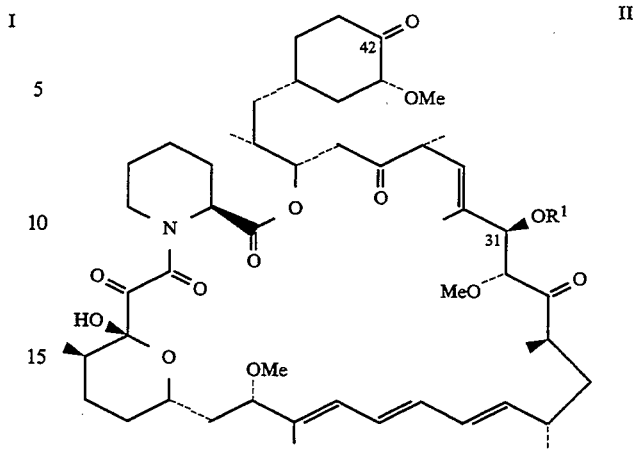

R¹ is

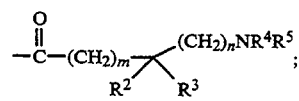

R² and R³ are each, independently, hydrogen, alkyl of 1–6 carbon atoms, arylalkyl of 7–10 carbon atoms, or may be taken together to form a cycloalkyl ring of 3–8 carbon atoms;

R⁴ and R⁵ are each, independently, hydrogen, alkyl of 1–6 carbon atoms, arylalkyl of 7–10 carbon atoms, or may be taken together to form a saturated heterocycle having 3–6 carbon atoms selected from the group consisting of piperidine, morpholine, thiomorpholine, piperazine, pyrazolidine, imidazolidine, and pyrrolidine, wherein the heterocyclic ring may be optionally mono-, di-, or tri-substituted with a group selected from alkyl of 1–6 carbon atoms and perfluoroalkyl of 1–6 carbon atoms;

wherein the aryl moiety of the arylalkyl group of R², R³, R⁴, and R⁵ is a phenyl, naphthyl, pyridinyl, quionlinyl, isoquinolinyl, thienyl, thionaphthyl, furanyl, benzofuranyl, benzodioxyl, benzoxazolyl, benzoisoxazolyl, indolyl, thiazolyl, isoxazolyl, pyrimidinyl, pyrazinyl, benzopyranyl, or benzimidazolyl group which may be optionally mono-, di-, or tri-substituted with a group selected from alkyl of 1–6 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO₃H, —PO₃H, and —CO₂H;

m=0–1; and
n=0–6;

or a pharmaceutically acceptable salt thereof, and a pharmaceutical carrier.

29. A compound which is rapamycin 42-ester with 2-(9H-fluoren-9-ylmethoxycarbonylamino)-2-methyl-propionic acid or a pharmaceutically acceptable salt thereof.

30. A compound which is rapamycin 42-ester with 1-(9H-fluoren-9-ylmethoxycarbonylamino)-cyclopentane carboxylic acid or a pharmaceutically acceptable salt thereof.

31. A compound which is rapamycin 42-ester with 1-(9H-fluoren-9-ylmethoxycarbonylamino)-cyclohexane carboxylic acid or a pharmaceutically acceptable salt thereof.

* * * * *